(12) United States Patent
Rudser

(10) Patent No.: US 10,153,655 B2
(45) Date of Patent: Dec. 11, 2018

(54) MULTIBAND WIRELESS POWER SYSTEM

(71) Applicant: HeartWare, Inc., Miami Lakes, FL (US)

(72) Inventor: John Rudser, Miami, FL (US)

(73) Assignee: HeartWare, Inc., Miami Lakes, FL (US)

( * ) Notice: Subject to any disclaimer, the term of this patent is extended or adjusted under 35 U.S.C. 154(b) by 0 days.

(21) Appl. No.: 15/976,475

(22) Filed: May 10, 2018

(65) Prior Publication Data

US 2018/0262041 A1     Sep. 13, 2018

Related U.S. Application Data

(63) Continuation of application No. 15/596,740, filed on May 16, 2017, now Pat. No. 9,991,734, which is a continuation of application No. 14/461,612, filed on Aug. 18, 2014, now Pat. No. 9,680,330.

(60) Provisional application No. 61/867,406, filed on Aug. 19, 2013.

(51) Int. Cl.
| | |
|---|---|
| *H02J 7/02* | (2016.01) |
| *H02J 50/90* | (2016.01) |
| *H02J 50/40* | (2016.01) |
| *H02J 50/12* | (2016.01) |
| *H02J 50/50* | (2016.01) |
| *A61F 2/02* | (2006.01) |

(52) U.S. Cl.
CPC .............. *H02J 7/025* (2013.01); *H02J 50/12* (2016.02); *H02J 50/40* (2016.02); *H02J 50/50* (2016.02); *H02J 50/90* (2016.02); *A61F 2/02* (2013.01)

(58) Field of Classification Search
CPC ....................................................... H02J 7/025
USPC ............................................................ 320/108
See application file for complete search history.

(56) References Cited

U.S. PATENT DOCUMENTS

| | | | |
|---|---|---|---|
| 8,159,090 B2 | 4/2012 | Greene et al. | |
| 8,169,185 B2 | 5/2012 | Partovi et al. | |
| 8,344,689 B2 | 1/2013 | Boguslayskij | |
| 8,417,359 B2 | 4/2013 | Tsai et al. | |
| 8,497,601 B2 | 7/2013 | Hall et al. | |

(Continued)

FOREIGN PATENT DOCUMENTS

| | | |
|---|---|---|
| CN | 1813396 A | 8/2006 |
| CN | 102149425 A | 8/2011 |

(Continued)

OTHER PUBLICATIONS

International Search Report and Written Opinion for Application No. PCT/US2014/051461 dated Nov. 28, 2014.

*Primary Examiner* — Suresh Memula
(74) *Attorney, Agent, or Firm* — Christopher & Weisberg, P.A.

(57) ABSTRACT

The present disclosure relates to a module for relaying power wirelessly to a device implanted in a user. The module may include a structure adapted to be worn by the user, a receiver configured to receive a first wireless power transmission at a first frequency, a transmitter configured to transmit a second wireless power transmission at a second frequency different from the first frequency, and a frequency changer configured to convert energy generated by the first wireless power transmission into energy for generating the second wireless power transmission. Each of the receiver, transmitter and frequency changer may be disposed on or in the structure.

12 Claims, 4 Drawing Sheets

(56) References Cited

U.S. PATENT DOCUMENTS

| | | |
|---|---|---|
| 8,536,736 B2 | 9/2013 | Abram et al. |
| 8,608,635 B2 | 12/2013 | Yomtov et al. |
| 9,642,958 B2 | 5/2017 | Zilbershlag et al. |
| 9,744,369 B2 | 8/2017 | Poon et al. |
| 9,855,376 B2 | 1/2018 | Bluvshtein et al. |
| 2010/0063347 A1 | 3/2010 | Yomtov et al. |
| 2010/0142509 A1* | 6/2010 | Zhu .................. H04B 1/1607 370/343 |
| 2011/0101788 A1 | 5/2011 | Sun et al. |
| 2011/0282415 A1 | 11/2011 | Eckhoff et al. |
| 2012/0032522 A1 | 2/2012 | Schatz et al. |
| 2012/0091950 A1 | 4/2012 | Campanella et al. |
| 2012/0248889 A1 | 10/2012 | Fukushi et al. |
| 2012/0262108 A1 | 10/2012 | Olson et al. |
| 2012/0277829 A1 | 11/2012 | Chow et al. |
| 2013/0214735 A1 | 8/2013 | Kong et al. |
| 2014/0152247 A1* | 6/2014 | Kim .................. H02J 5/005 320/108 |
| 2016/0220828 A1 | 8/2016 | Yan Poon et al. |
| 2016/0233715 A1* | 8/2016 | Lee .................. H02J 17/00 |
| 2017/0216508 A1 | 8/2017 | Zilbershlag et al. |
| 2017/0271919 A1 | 9/2017 | Von Novak, III et al. |

FOREIGN PATENT DOCUMENTS

| | | |
|---|---|---|
| CN | 102709997 A | 10/2012 |
| CN | 103222199 A | 7/2013 |

\* cited by examiner

FIGURE 1          100

MULTIBAND WIRELESS POWER SYSTEM

CROSS-REFERENCE TO RELATED APPLICATION

This application is a Continuation of U.S. patent application Ser. No. 15/596,740, filed May 16, 2017 and is related to and claims priority to U.S. Utility patent application Ser. No. 14/461,612, filed Aug. 18, 2014, entitled MULTIBAND WIRELESS POWER SYSTEM, now Issued U.S. Pat. No. 9,680,330, issued Jun. 13, 2017 and is related to and claims priority to U.S. Provisional Patent Application Ser. No. 61/867,406, filed Aug. 19, 2013, entitled MULTIBAND WIRELESS POWER SYSTEM, the entirety of which is incorporated herein by reference.

STATEMENT REGARDING FEDERALLY SPONSORED RESEARCH OR DEVELOPMENT n/a

TECHNICAL FIELD

The present invention relates to a transcutaneous energy transfer (TET) system, and more particularly to a device for transferring or relaying power wirelessly within a TET system, as well methods of operating the system and/or device.

BACKGROUND

TET systems are used to supply power to devices such as pumps implanted internally within the human body. An electromagnetic field generated by a transmitting coil outside the body can transmit power across a cutaneous (skin) barrier to a magnetic receiving coil implanted within the body. The receiving coil can then transfer the received power to the implanted pump or other internal device and to one or more batteries implanted within the body to charge the battery.

One of the challenges presented by TET systems is to provide sufficient power to the internal device to enable continuous operation of the internal device. For this purpose, the TET system may include an implanted battery that stores power for operating the internal device. However, the implanted battery's supply is limited and may need to be recharged frequently. The TET system may also, or alternatively, include an external TET power unit to supply the internal device's entire power demand. However, the external TET power unit also has a limited supply and may need to be recharged regularly. Moreover, some activities such as showering or swimming may preclude wearing the external TET power unit.

Constant recharging of an external TET power unit, as well as an implanted battery is an inconvenience for a user with the internal device(s). Ordinarily, the external TET power unit must be plugged into a charging station in order to be recharged. A user may have to wait for the unit to sufficiently charge before wearing the unit. Alternatively, the user may replace the battery in the external TET power unit with a fully charged battery.

It is therefore desirable to improve upon present TET systems to make recharging of external TET power units and implanted batteries more convenient for the user.

SUMMARY

One aspect of the present disclosure provides for a module for relaying power wirelessly to a device implanted in a user. The module may include a structure adapted to be worn by the user, a receiver configured to receive a first wireless power transmission at a first frequency, a transmitter configured to transmit a second wireless power transmission at a second frequency different from the first frequency, and a frequency changer electrically coupled to each of the transmitter and receiver and configured to convert energy generated by the first wireless power transmission into energy for generating the second wireless power transmission. Each of the receiver, transmitter and frequency changer may be disposed on or in the structure. In some examples, the first frequency and second frequency may belong to different frequency bands. In other examples, the first frequency may be more than twice as great as the second frequency. In further examples, the respective frequencies may be selected for different distances, and may be selected for different media.

The module may further include a control circuit configured to determine a wireless power transmission efficiency of the receiver and to dynamically adjust the first frequency based on said determination. The control circuit may determine wireless power transmission efficiency based on a measured peak signal at the receiver. The module may additionally or alternatively include a battery electrically coupled to the receiver and a control circuit for determining whether to store energy generated by the first wireless power transmission in the battery, to relay the energy generated by the first wireless power transmission to the transmitter, or both.

The structure of the module may include a housing, the receiver and transmitter being disposed within the housing. The module may be adapted to be worn by the user such that the receiver is disposed at an end of the housing facing away from the user and the transmitter is disposed at an end of the housing facing towards the user.

Another aspect of the disclosure provides for a transcutaneous energy transfer system for delivering power to a device implanted within a user, including a module such as the module described above, and further including a remote power source electromagnetically couplable to the module and configured to wirelessly transmit the first wireless power transmission to the module, as well as an implanted receiver adapted for implantation within the user, inductively couplable to the module and electrically coupleable to the implanted device, and configured to receive the second wireless power transmission from the module. Such system may also include an external battery electrically coupled to the module, used to store energy received from the first wireless power transmission and to provide the stored energy to the transmitter to generate the second wireless power transmission. Such system may further include an implanted battery electrically coupled to the implanted receiver, used to store energy received from the second wireless power transmission and to provide the stored energy to the implanted device in order to power the device. The implanted battery may store energy when the module is worn by the user, and may power the implanted medical device when the external charging module is not worn by the user. The external battery may store energy when the module is electromagnetically coupled to the remote power source, and may provide stored energy to the transmitter when the module is not electromagnetically coupled to the remote power source.

A further aspect of the disclosure provides for an apparatus for relaying power wirelessly, having a plurality of receiver circuits adapted to receive a wireless power at a respective resonant frequency of the receiver circuit, a transmitter circuit adapted to transmit wireless power at a selected resonant frequency, and a plurality of frequency changers. Each frequency changer may be electrically coupled to an output of a respective receiver circuit and to an input of the transmitter circuit, and configured to convert the frequency of the wireless power received at the respective receiver circuit to the selected frequency. In some examples, each receiver circuit may be adapted to receive wireless power at a different frequency. The apparatus may be included in a wireless energy which may further include a plurality of remote transmitter circuits. Each remote transmitter circuit may be adapted to generate and transmit wireless power at the resonant frequency of a corresponding receiver circuit at the apparatus.

Yet a further aspect of the disclosure provides for a transcutaneous energy transfer system having an implanted wireless power receiver electrically couplable to an implanted medical device, a remote power source generating power sufficient to operate the implanted medical device, and one or more wireless power relay apparatuses configured to relay power from the remote power source en route to the implanted wireless power receiver. Each apparatus may further include a receiver adapted to receive an incoming wireless power transmission at a first frequency, a transmitter adapted to transmit an outgoing wireless power transmission at a second frequency; and a frequency changer electrically coupled to the transmitter and to the receiver, and configured to convert energy generated by the incoming wireless power transmission into energy for generating the outgoing wireless transmission. A plurality of apparatuses may be serially electromagnetically coupled to one another such that the wireless power transmitted by an upstream apparatus is the wireless power received at a serially electromagnetically coupled downstream apparatus. The implanted wireless power receiver may further be adapted to receive the wireless power generated by a farthest downstream wireless power relay apparatus.

In some examples of the system, the farthest downstream wireless power relay apparatus may include an external battery electrically coupled to the receiver. The external battery may be used to temporarily store charge (e.g., when the farthest downstream wireless power relay apparatus is electromagnetically coupled to a respective upstream apparatus) and generate power for driving the transmitter at the second frequency using said stored charge (e.g., when the farthest downstream wireless power relay apparatus is not electromagnetically coupled to a respective upstream apparatus). Similarly, an implanted battery may be electrically coupled to the implanted wireless power receiver and to the implanted medical device to temporarily store charge (e.g., when the farthest downstream wireless power relay apparatus is operatively coupled to the implanted wireless power receiver) and to generate power sufficient for operating the implanted medical device (e.g., when the farthest downstream wireless power relay apparatus is not operatively coupled to the implanted wireless power receiver, when the farthest downstream wireless power relay apparatus does not on its own generate sufficient power for operating the implanted medical device, etc.).

Yet another aspect of the disclosure provides for a method of relaying power wirelessly to a device implanted in a user, involving, providing a structure adapted to be worn by the user, receiving a first wireless power transmission at a first frequency at a receiver disposed on or in the structure, transmitting a second wireless power transmission at a second frequency different from the first frequency from a transmitter disposed on or in the structure, and converting energy generated by the first wireless power transmission into energy for generating the second wireless power transmission at a frequency changer electrically coupled to the receiver and the transmitter and disposed on or in the structure. In some examples of the method, the first wireless power transmission may be transmitted over a distance that is greater than the distance that the second wireless power transmission is transmitted. Also, in some examples of the method, the first wireless power transmission may be transmitted through a medium that is different than the medium through which the second wireless power transmission is transmitted.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
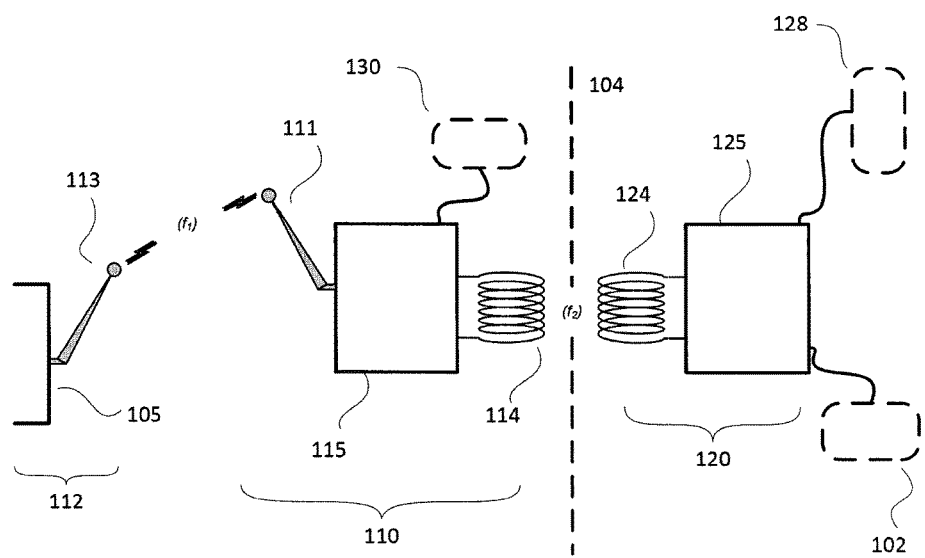
FIG. 1 is a block and schematic diagram illustrating components of a multiband TET system in accordance with an embodiment of the invention.
Figure 2:
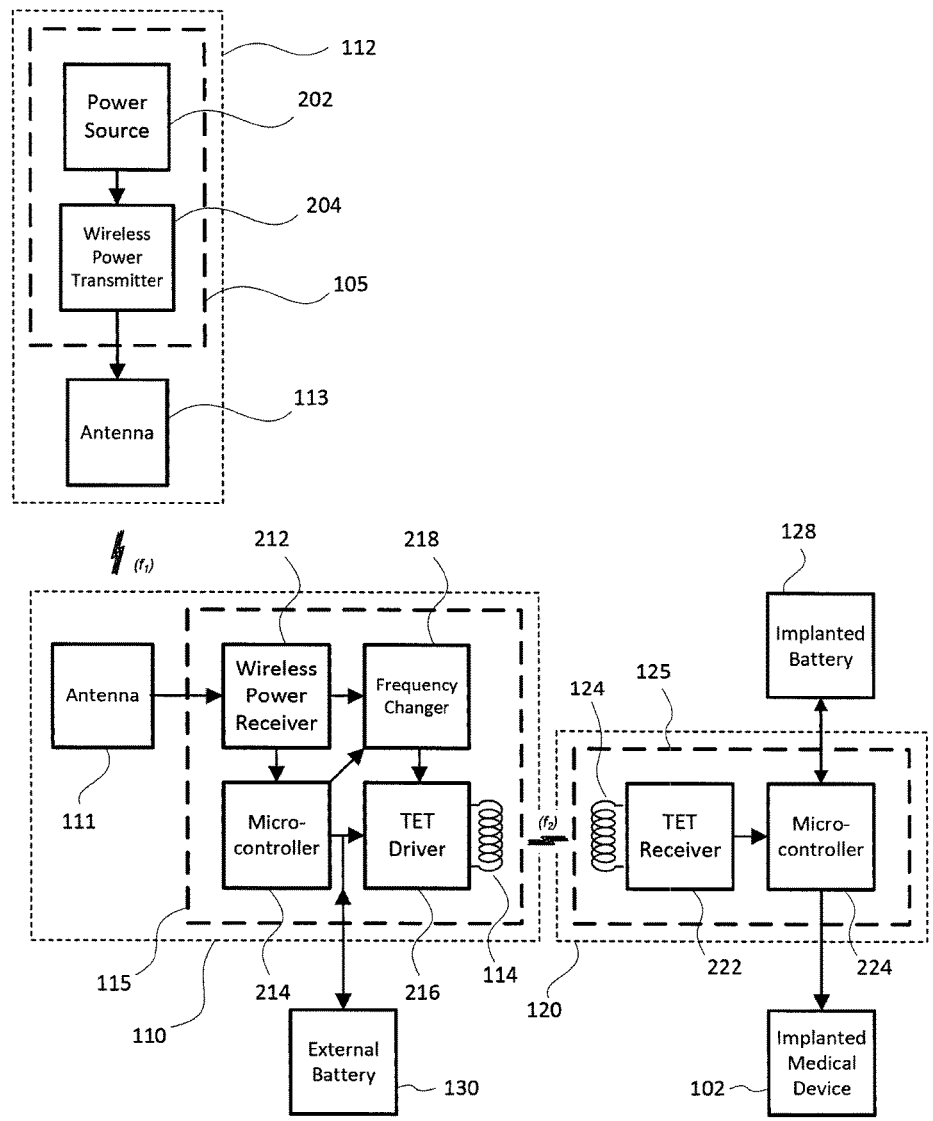
FIG. 2 is a block and schematic diagram further illustrating components of each an external and implanted module of the multiband TET system of FIG. 1 in accordance with an embodiment of the invention.

FIGS. 1 and 2 schematically illustrate a multiband transcutaneous energy transfer (TET) system 100 used to supply power to an implanted therapeutic electrical device 102 in an internal cavity within the body, i.e., below the skin of a user 104. The implanted electrical device 102 can include a pump such as for use in pumping blood as a ventricular assist device ("VAD"), for example. The implanted electrical device 102 can include controlling circuitry to control, for example, a pump.

As depicted in FIG. 1, the multiband TET system 100 includes an external module 110 having a primary power coil circuit 114, associated circuitry (shown in greater detail in FIG. 2) and an antenna 111 for wirelessly receiving power from a remote power source 112 electromagnetically coupled to the external module 110. The external module components are all disposed in or on a structure that is mountable to (e.g., wearable by) the user 104. For example, the structure may include a housing 115 which is small enough to be carried by the user. The housing 115 may optionally be equipped with devices for affixing it to the user as, for example, belt loops adapted to secure the housing to a belt worn by the user, or straps for securing it to the user's body. Alternatively the housing 115 may be secured to the user's body by external devices such as a bandle, clothing, or an adhesive.

An internal module 120 implanted underneath the skin of the user 104 has a secondary power coil circuit 124, associated circuitry disposed in one or more housings 125 and an output cable for supplying power to the implanted electrical device 102. Power is transferred from the primary coil 114 to the secondary coil 124 by means of inductive electromagnetic coupling, i.e., via interaction of a magnetic field overlapping the primary 114 and secondary 124 coils. The voltage across each coil can be large, for example, peak-to-peak voltages of 100 V to 400 V are not uncommon. To reduce losses due to skin effect, the primary coil 114 can be fabricated using Litz wire, in which the primary coil 114 is made up of relatively thin, insulated wires twisted or woven together.

In order to facilitate power transfer between the external and implanted modules, the antenna 111 of the external module 110 may be disposed at an "outward" facing side of the external module (i.e., facing away from the user 104), whereas the primary coil 114 may be disposed at an "inward" facing side (i.e., facing towards the user 104).

The external module 110 is further electrically connected to an external rechargeable battery 130 or charge accumulator. The battery 130 may be included in or on the structure or may be kept separate from the structure. The external battery may serve as a backup power source to the remote power source 112. For example, the battery 130 may supply power to the primary coil 114 of the module in order to generate wireless power in case power transmission to the external module 110 is interrupted or in case the power demand of the implanted device 102 changes. When the backup external battery 130 is sufficiently charged, the user is free to move out of range of the remote power source 112.

The implanted module 120 is also connected to a rechargeable battery 128 or charge accumulator for supplying power to the implanted electrical device 102. As with the external battery 130, and as described in greater detail below, the implanted battery 128 may serve as a backup in case power transmission from the remote power source 112 to the external module 110 is interrupted, in case power transmission between the external 110 and implanted 120 modules is interrupted, or in case of changes in power demands. With the implanted battery 128 as a backup, the external TET module 110 can be disconnected when the user bathes or performs other activities.

In the example of FIG. 1, the optimal frequency for wireless power transmission may differ between the first stage (i.e., from the remote power source 112 to the external module 110) and the second stage (i.e., from the external module 110 to the implanted module 120). One such reason for the difference in optimal frequencies may be a difference in the distance for each stage of wireless power transfer. For example, power transferred from the remote power source 112 may travel several meters (e.g., between about 1 and about 10 meters) to the external module 110, whereas power transferred between the external 110 and implanted 120 modules may travel on the order of millimeters (e.g., between about 5 and about 200 millimeters). Another reason for the difference in optimal frequencies may be a difference in medium for each stage of wireless power transfer. For example, power transferred from the remote power source 112 may travel from one room of a building or other structure (e.g., through wood, concrete, drywall, rock, air, etc., or any combination of the above) to the external module 110, whereas power transferred between the external 110 and implanted 120 modules may travel through only air and/or the patient's skin. To summarize, changes in either distance or medium may affect the optimal frequency at which power is transferred wirelessly.

In order to accommodate these changes, the antenna 111 may receive wireless energy at a selected first frequency $f_1$, whereas the primary and secondary coils of the multiband TET system 100 may transfer and receive, respectively, wireless energy at a selected second frequency $f_2$. In some instances, the first and second frequencies may belong to separate frequency bands. For purposes of this disclosure, the term "frequency band" may refer to a predefined range of frequencies, such as those set forth by the American Radio Relay League (ARRL) or Institute of Electrical and Electronics Engineers (IEEE). "Separate" frequency bands may refer to two non-overlapping predefined ranges of frequencies. In some examples, the lowest frequency of one of the separate bands may be more than double the highest frequency of the other band.

Optimizing the strength of relayed wireless power may take several factors into account, including both the strength of the relayed power, as well as the safety of the user. For example, the first stage of wireless power transfer in the example of the TET system of FIG. 1 may travel a significant distance (e.g., on the order of several meters). As such, the frequency $f_1$ at the first stage may be selected to ensure that the power is not adversely affected by the distance traveled. For further example, the final stage of wireless power transfer travels through the user's skin and tissue. As such, the frequency $f_2$ at the final stage may be selected to ensure safe penetration of the surface of the user's skin, while avoiding risks to the user's health (internal organs), and overheating or radiation for instance if the primary and secondary coils are not properly aligned. Frequencies $f_1$ and $f_2$ may fall within the radio frequency (RF) spectrum, and may range on the order of kilohertz (kHz) to megahertz (MHz) depending on the particular factors (e.g., distance, relative orientation of the transmitting and receiving elements, etc.) impacting the transmitted power. For instance, the frequency $f_1$ at the first stage may be between about 10 kHz and about 3000 MHz, whereas the frequency $f_2$ at the second stage may be between about 10 kHz and about 500 kHz.

FIG. 2 is a functional block diagram illustrating electrical components of the multiband TET system 100 of FIG. 1. As illustrated therein, the remote power source 112 of the system 100 includes a power source 202 and a wireless power transmitter 204 electrically coupled to the power source 202 and remote antenna 113. The transmitter 204 and antenna 113 form a tank circuit having one or more capacitive elements coupled to the inductive element and series resistance of the antenna. Using the power received from the power source 202, the wireless power transmitter 204 drives the remote antenna 113, which includes, to resonate at the resonant frequency $f_1$ dictated by the tuned capacitive/inductive properties of the transmitter/antenna, such that wireless power is transmitted from the remote antenna 113 to the antenna 111 of external module 110 at the first frequency $f_1$.

The external module 110 includes a wireless power receiver 212 electrically coupled to the antenna 111 thereby forming a tank circuit (comparable to the tank circuit of the remote power source 112) that is adapted to generate power from the wireless energy transmitted by the remote power source 112 by means of electromagnetic coupling. The power generated by the wireless power receiver 212 is at the resonant frequency $f_1$. In some examples, the first frequency $f_1$ may be dynamically adjusted in order to optimize efficiency of the wireless power transfer. Efficiency may be affected by several factors, such as the relative distance and relative orientation between the antenna 111 and remote antenna 113, as well as the medium or media between the antenna 111 and remote antenna 113. Determining the efficiency of the wireless energy transfer may be based on a peak signal measured at the receiver 212 and may further be based on known characteristics of a load at the receiver 212.

Such measurements and known information may be relayed between the external module 110 and the remote power source 112, for example using RF telemetry signals.

The associated circuitry of the external module further includes a microcontroller 214, a power amplifier/driver 216, and a frequency changer 218. Power received from the wireless transmitter 201 at frequency $f_1$ is processed at the frequency changer 218 and provided to the implanted module 120 by the TET driver 216 as controlled by microcontroller 214. The frequency changer may utilize a frequency multiplier, doubler or mixer to raise or lower the frequency of the power generated at the external module 110 from $f_1$ and $f_2$. Frequencies $f_1$ and $f_2$ may belong to different frequency bands.

The microcontroller 214 may also be configured to determine and control the source or sources of power from which the wireless power at the primary coil 114 is generated. The primary coil 114 may be powered from the remote power source 112, the external battery 130, or both. For example, when the external module 110 is communicatively coupled to the remote power source 112, the microcontroller 214 may determine to use the power received from the remote power source 112. Additionally, any excess power not used in driving the primary coil 114 may instead be stored at the external battery 130. When the remote power source 112 is not coupled to the external module 110, or during periods of peak power demand, the microcontroller 214 may determine to use charge stored at the external battery 130 to drive the primary coil 114. The microcontroller 214 may operate one or more switches to route electrical current from the selected source of power. The microcontroller 214 may further control the routing of wireless power from the remote power source to either or both the primary coil 114 and the external battery 130, thereby coordinating the charging of the battery 130 with the driving of the primary coil 114. For example, commonly owned U.S. Pat. No. 8,608,635, the disclosure of which is hereby incorporated herein in its entirety, describes a method of operation of a TET system the flow of electrical power from the external module to the implanted module is precisely metered according to the instantaneous power demand of the implanted device so that power is not drawn from the implanted battery during normal operation of the implanted device.

The transmission frequency of the primary coil 114 may be preset to, or in some examples dynamically set to, a desired transmission frequency (frequency $f_2$ in the example of FIGS. 1 and 2) in order to optimize power transmission to the secondary coil of the implanted module 120. The microcontroller 214 may be capable of controlling the frequency changer 218 in order to dynamically adjust the frequency of the received energy at the wireless power receiver 212 to the desired transmission frequency $f_2$. In those examples where the desired frequency $f_2$ is dynamically set and updated, power optimization between the primary and secondary coils, like power optimization between the remote power source and external module, may be based on measured peak signal values and known load characteristics at the downstream module (which in the present example is the implanted module 120) and may be communicated upstream via RF telemetry so that the upstream module's controller (in this case the microcontroller 214 of the external module 110) controls the wireless power transmission frequency.

The implanted module 120 includes a TET receiver 222 and a microcontroller 224 electrically coupled to the receiver. The TET receiver 222, along with the secondary coil 124 forms a tuned resonant circuit set to the transmission frequency $f_2$. The secondary coil 124, like the primary coil 114, may be fabricated using Litz wire. The TET receiver 222 further includes rectifier circuitry (not shown), such as active switching or a diode bridge, for converting an alternating current ("AC") voltage at the secondary coil into a direct current ("DC") voltage. DC power output from the TET receiver 222 is supplied to the microcontroller 224, the implanted battery 128 and an implanted electrical device 102. The implanted electrical device 102 can include one or more of a variety of devices such as a VAD blood pump. The power demands of the implanted electrical device 102 are such that the implanted battery 128 can only power the device for a limited amount of time (e.g., a few hours, a day, etc.). In such case, the implanted battery 128 does not serve as a main power source for the implanted device, but rather as a backup power source used to supply power for relatively short periods of time in case of an interruption in the transmission of power to the implanted module 120. For example, the implanted module 120 can rely on battery power when the user takes off the external module 110, such as in order to take a shower.

In each of the above examples, the wireless power received at the secondary coil 124 of the implanted module could be used immediately to power the implanted device, temporarily stored at the implanted battery 128 for future use, or both. Thus, some or all of the power can be routed to the implanted device 102, whereas remaining power can be routed to the implanted battery 128. The implanted microcontroller 224 may be configured to determine whether to use or store the received wireless power. For instance, the controller may determine to store received power when the external module 110 is worn by the user 104, and to power the implanted medical device 102 using the stored charge when the external module 110 is removed from the user 104. Determining whether the external module 110 is being worn or removed from the user 104 may be determined based on whether any electrical current is present at the secondary coil.

In other examples, control over storing and/or use of wireless power may be dictated by changes in power demands from the implanted device. For instance, if the implanted device requires an additional burst of power, the controller (either external 214 or implanted 224) may determine to provide the extra power using stored charge (either in the external or implanted battery). Such methods of control are described in detail in commonly owned U.S. Pat. No. 8,608,635. For further instance, if a temperature sensor indicates that an implanted or external electronic component is operating inefficiently (overloaded, overheated, not aligned), the controller may determine to cease wireless power transmission at least temporarily and continue operating the implanted medical device 102 using energy from the implanted battery 128. Such determinations may be made regardless of electrical, communicative, or inductive coupling between components of the TET system.

The external module 110 may include additional components not shown in FIG. 2, including, although not limited to, a thermal sensor, an over-voltage protection (OVP) circuit, and an RF telemetry system. These components and their operation are described in greater detail in commonly owned U.S. Pat. No. 8,608,635.

The multiband TET system illustrated in FIGS. 1 and 2 includes only two stages: a first stage from the remote power source 112 to the external module 110; and a second stage from the external module 110 to the implanted module 120. Other multiband TET systems may include additional stages for transferring/relaying power wirelessly. The additional stages may be in configured in series or in parallel with one another, or may include any combination of serial/parallel connections.

Figure 3:
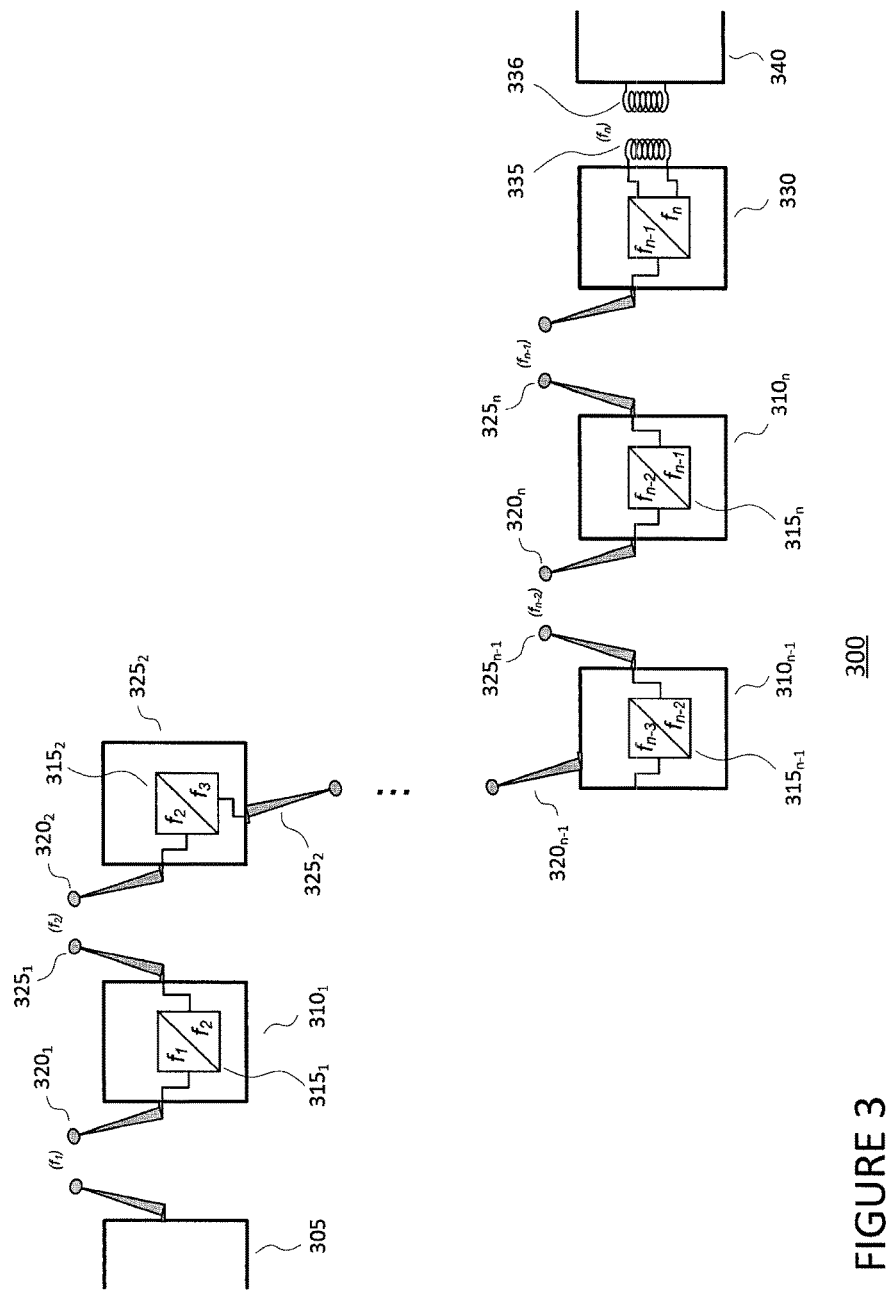
FIG. 3 is a block and schematic diagram further illustrating components of a multiband TET relay system in accordance with a further embodiment of the invention.

The example multiband TET system 300 of FIG. 3 illustrates a serially connected system including several wireless charging relay stations $310_1$-$310_n$ as wireless repeaters to relay power wirelessly from a remote power source 305 to an external module 330. The relay stations $310_1$-$310_n$ communicate with one another serially in an upstream-to-downstream order. Thus, the first relay station $310_1$ passes power wirelessly to the next downstream station $310_2$ and so on to the farthest downstream station $310_n$. Each relay station $310_1$-$310_n$ includes a receiver antenna $320_1$-$320_n$ and transmitter antenna $325_1$-$325_n$ for relaying the wireless power, as well as a frequency changer $315_1$-$315_n$ for converting the frequency of the received power to a new frequency for the subsequent stage of transmission. The frequency of each relay stage may be fixed or preset based on known characteristics of the system & environment (e.g., approximate distances and/or media between each relay station). Alternatively, each relay station may include a respective control circuit (not shown) for dynamically controlling the frequency and/or frequency band of each relayed stage based on certain factors, such as the distance, medium and/or relative orientation between each respective transmitter/receiver pair. Whether the frequency changer $315_1$-$315_n$ of a given station is instructed by the control circuit to change the frequency of a given stage, and to what frequency that stage is changed, may depend on those factors. In such an example, a downstream relay station may send telemetry signals representative of the power received, and the upstream relay station may receive these signals and adjust the transmission parameters in order to maximize power received by the downstream relay station.

Operation of the serial multiband TET 300 begins with external remote power source 305 generating and transmitting power wirelessly to the first wireless charging relay station $310_1$ at a first frequency $f_1$. The first wireless charging relay station $310_1$ receives the power, then converts it to a second frequency $f_2$, and then transmits the converted power at the second frequency $f_2$ to the second wireless charging relay station $310_2$. As with the first station, the second station, and each of the subsequent stations in turn, receives the power, converts it to a different frequency, and transmits it on to the next downstream station until it is received at the external module 330 (at frequency $f_{n-1}$) and relayed to the implanted module 340 via primary and secondary coils 335/336 (at frequency $f_n$). Use of serially connected stations thereby increases the overall distance over which power may be transmitted wirelessly.

As in the example embodiment of FIGS. 1 and 2, the second frequency $f_2$ may be different than the first frequency $f_1$. Likewise, each power transfer stage may be set to a different frequency. Alternatively, in some instances, the frequencies of some or all of the power transfer stages may be the same, with each relay station increasing the overall distance of wireless power transmission for the TET system.

Figure 4:
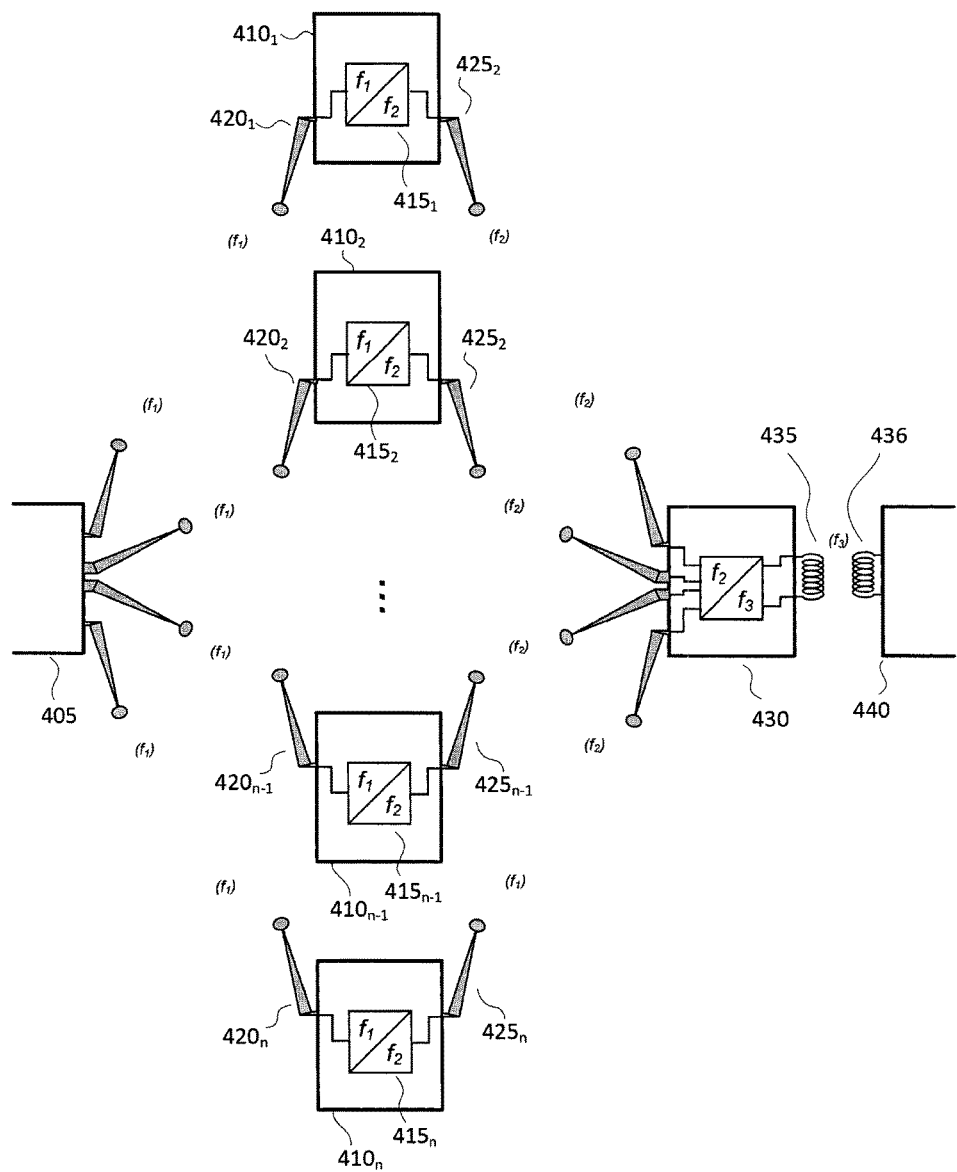
FIG. 4 is a block and schematic diagram further illustrating components of another multiband TET relay system in accordance with yet another embodiment of the invention.

The example multiband TET system of FIG. 4 illustrates a system connected in parallel including several wireless charging relay stations $410_1$-$410_n$. As with the example of FIG. 3, each station $410_{1-n}$ includes each of a receiver antenna $420_1$-$420_n$, a transmitter antenna $425_1$-$425_n$, a frequency changer $415_1$-$415_n$, and a control circuit (not shown) with capabilities similar to the analogous components described in connection with FIG. 3.

Operation of the parallel multiband TET 400 begins with an external power source 405 generating and transmitting power wirelessly to each of the wireless charging relay stations $410_1$-$410_n$ at a first frequency $f_1$. Each wireless charging relay station $410_1$-$410_n$ receives power transmitted at frequency $f_1$, then converts it to a second frequency $f_2$, and then transmits it at the second frequency $f_2$ to the external module 430, which then relays it to the implanted module 440 at the third frequency $f_3$ via primary and secondary coils 435/436. As with the example of FIG. 3, the first and second frequencies may be the same or different. Power at each receiver of the external module may be combined in the external receiver to provide more power to the implanted module. Use of charging stations connected in parallel thereby increases the amount of power that can be transmitted to the external module without increasing the amount of power handled by any of the relay stations.

In another example of parallel relay of wireless power, the external module may include a separate frequency changer for each relay station coupled thereto. In such an example, the external module may be capable of receiving wireless power at multiple frequencies, such as if each relay station is set to a different resonant frequency. For example, each relay station may be a different distance from the external module, or separated by a different medium, or both. In such a case, each receiver of the external module would be electrically coupled to the input of a respective frequency changer, and each frequency changer would change the frequency of the respective received wireless power to a common frequency before combining all of the received power. In order to combine the wireless power received at each receiver, the external module may be configured to convert all received power to a common AC frequency, or to convert all received power to DC and using the converted DC power to drive the primary coil of the external module.

In further examples of parallel relay of wireless power, each relay station may receive power from a separate power source. This in turn permits for improved charging while using smaller power sources in the charging process.

In yet further examples of parallel relay of wireless power, one or more external power sources may be configured to generate power at different resonant frequencies (for example, at least two different frequencies). The power may then be relayed to different parallel relay stations having receivers tuned to the respective different frequencies. Along the same line, the external module may be equipped with multiple receivers, so as to receive relayed power from each of the various parallel relay stations. In such a situation, the external module may include multiple frequency changers, each coupled to a respective receiver, as described above.

In yet further examples of parallel relay, instead of including multiple receivers in the external module, the implanted module itself may be equipped with the multiple receivers. In such examples, the implanted module may further be equipped with circuitry to combine power received from multiple sources inside the user. In those examples, converting the power to a common AC frequency would not be necessary, since all of the power generated at the implanted receiver would be rectified to a DC voltage for storage in the implanted battery and/or operating the implanted medical device.

In some examples, parallel and serial systems may be used in combination with one another. The relay stations rely on intelligent switching and/or adapting techniques known in the art in order to efficiently transfer power from the power source to the external module, even if the external module is constantly moving from location to location, such as if the user were to walk from one end of a room or building to the opposite end while wearing the external module. Such techniques would include changes in the frequency of a transferred signal between stations, or changes in which station(s) the signal is relayed to efficiently transmit it to the external module. Altogether, the above techniques would allow the user to charge or recharge the external module without having to remove the unit or to remain stationary. Simply put, the present disclosure is not limited in the manner by which relay stations are arranged or organized or by the particular frequency (or frequency band) received and/or transmitted at any given station.

While the above disclosure describes a TET system having discrete modules, each module containing all associated circuitry within a unitary structure (i.e., a housing), it will be recognized that the disclosure is similarly applicable to any apparatus for wireless power relay, even without such a unitary structure. For instance, the external module of FIGS. 1 and 2 may be adapted to include primary coils, power receiving circuitry, frequency changers, external batteries, etc., contained in or mounted to different structures (e.g., a primary coil worn on the patient's chest and an external battery secured to the patient's belt, etc.). The same is true of the implanted module. For instance, each of the secondary coil, the implanted microcontroller, rectifier, and implanted battery may be housed together or separately in any desired combination.

Furthermore, while the above disclosure generally describes a TET system for use in a user having an implanted VAD, it will be recognized that the disclosure is similarly applicable to any system having each of a non-transcutaneous and a transcutaneous stage of wireless power delivery. As such, the disclosure is similarly applicable for driving any implanted device, and also applicable for driving a device implanted in any human patient or other animal.

Yet further, while the above disclosure primarily addresses advancements in transcutaneous wireless power transfer systems, it will be recognized that the present disclosure may has broader application and benefits in other wireless power transfer systems. For instance, application of the present disclosure may be beneficial within any system having multiple stages of wireless power transfer of substantially varying lengths (e.g., meters as compared to centimeters, miles as compared to yards, etc.).

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A module for relaying power wirelessly to an implanted device, comprising:
an external module;
a receiver configured to receive a first wireless power transmission at a first frequency;
a transmitter configured to transmit a second wireless power transmission at a second frequency different from the first frequency;
a frequency changer electrically coupled to each of the transmitter and the receiver, the frequency changer configured to convert energy generated by the first wireless power transmission into energy for generating the second wireless power transmission; and
at least one from the group consisting of the receiver, transmitter, and frequency changer are disposed at least one from the group consisting of on the external module and in the external module.

2. The module of claim 1, wherein each of the first frequency and second frequency belong to different frequency bands.

3. The module of claim 1, wherein the first frequency is selected for wireless power transmission at a first distance and the second frequency is selected for wireless power transmission at a second distance shorter than the first distance.

4. The module of claim 1, wherein the first frequency is selected for wireless power transmission through a first medium and the second frequency is selected for wireless power transmission through a second medium different than the first medium.

5. The module of claim 1, further comprising a control circuit configured to determine a wireless power transmission efficiency of the receiver and to dynamically adjust the first frequency based on said determination.

6. The module of claim 5, wherein the control circuit is configured to determine wireless power transmission efficiency based on a measured peak signal at the receiver.

7. The module of claim 1, wherein the first frequency is more than twice as great as the second frequency.

8. The module of claim 1, further comprising a battery electrically coupled to the receiver and a control circuit for determining whether to store energy generated by the first wireless power transmission in the battery, to relay the energy generated by the first wireless power transmission to the transmitter, or both.

9. A transcutaneous energy transfer system, comprising:
an implanted wireless power receiver;
a remote power source; and
a wireless power relay apparatus configured to relay power from the remote power source to the implanted wireless power receiver, the apparatus comprising:
a receiver configured to receive an incoming wireless power transmission at a first frequency;
a transmitter configured to transmit an outgoing wireless power transmission at a second frequency; and
a frequency changer electrically in communication with the transmitter and to the receiver, the frequency changer being configured to convert energy generated by the incoming wireless power transmission into energy for generating the outgoing wireless transmission.

10. The system of claim 9, wherein the wireless power relay apparatus includes a plurality of apparatuses electromagnetically coupled to one another, wherein the wireless power transmitted by an upstream apparatus of the plurality of apparatuses is the wireless power received at a downstream one of the plurality of apparatuses, and wherein the implanted wireless power receiver is configured to receive the wireless power generated by a farthest downstream wireless power relay apparatus of the plurality of apparatuses.

11. The system of claim 10, wherein the farthest downstream wireless power relay apparatus of the plurality of apparatuses further comprises an external battery electrically coupled to the receiver, the external battery being used to:
temporarily store charge when the farthest downstream wireless power relay apparatus of the plurality of apparatuses is electromagnetically coupled to a respective upstream apparatus of the plurality of apparatuses; and generate power for driving the transmitter at the second frequency using the stored charge when the farthest downstream wireless power relay apparatus of the plurality of apparatuses is not electromagnetically coupled to a respective upstream apparatus of the plurality of apparatuses.

12. The system of claim 10, further comprising an implanted battery electrically coupled to the implanted wireless power receiver, the implanted battery used to:
- temporarily store charge when the farthest downstream wireless power relay apparatus of the plurality of apparatuses is operatively coupled to the implanted wireless power receiver; and
- generate power when at least one from the group consisting of the farthest downstream wireless power relay apparatus of the plurality of apparatuses is not operatively coupled to the implanted wireless power receiver and when the farthest downstream wireless power relay apparatus of the plurality of apparatuses does not on its own generate power.

\* \* \* \* \*